United States Patent [19]

Cliffe et al.

[11] Patent Number: 5,164,385
[45] Date of Patent: Nov. 17, 1992

[54] AZETIDINE DERIVATIVES AND HYPOTENSIVE COMPOSITIONS THEREOF

[75] Inventors: Ian A. Cliffe, Slough; Alan C. White, Englefield Green, both of England

[73] Assignee: John Wyeth & Brother, Ltd., Maidenhead, England

[21] Appl. No.: 756,410

[22] Filed: Sep. 9, 1991

[30] Foreign Application Priority Data

Sep. 12, 1990 [GB] United Kingdom ............... 9019942

[51] Int. Cl.$^5$ ............... A61K 31/395; C07D 203/14
[52] U.S. Cl. ........................ 514/210; 548/950
[58] Field of Search ............. 514/210; 548/950

[56] References Cited

U.S. PATENT DOCUMENTS

| | | | |
|---|---|---|---|
| 5,026,857 | 6/1991 | Schohe et al. | 514/319 |
| 5,053,430 | 10/1991 | Grauert et al. | 514/630 |
| 5,075,303 | 12/1991 | Cliffe | 514/218 |

FOREIGN PATENT DOCUMENTS 0361300 9/1989 European Pat. Off. .

Primary Examiner—Joseph Paul Brust
Assistant Examiner—Jacqueline Haley
Attorney, Agent, or Firm—Arthur G. Seifert

[57] ABSTRACT

Azetidine derivatives of formula

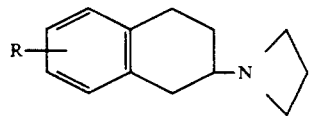

(I)

and their pharmaceutically acceptable acid addition salts are disclosed. In the formula R is hydrogen or one or more specified substituents. The compounds have hypotensive activity. Some are also 5-HT$_{1A}$ agonists.

6 Claims, No Drawings

AZETIDINE DERIVATIVES AND HYPOTENSIVE COMPOSITIONS THEREOF

This invention relates to azetidine derivatives, to processes for their preparation, to their use and to pharmaceutical compositions containing them.

The compounds of the invention are those of the general formula

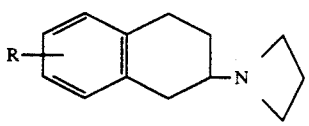
(I)

and the pharmaceutically acceptable acid addition salts thereof.

In formula (I)

R is hydrogen or one or more same or different substituents selected from hydroxy, lower alkyl, aryl(lower)alkyl, lower alkoxy, aryl(lower)alkoxy, halogen, halo(lower)alkyl, halo(lower)alkoxy, methylenedioxy, nitro, lower alkylcarbonyloxy, aryl(lower)alkylcarbonyloxy, lower alkoxycarbonyl, aminocarbonyl, amino, (lower)alkylamino, di(lower)alkylamino or acylamino (e.g. lower alkanoylamino or loweralkyl-sulphonyloxyamino).

The term "lower" as used herein means that the radical referred to contains 1 to 6 carbon atoms. Preferably such radicals contain 1 to 4 carbon atoms.

Examples of lower alkyl are methyl, ethyl, propyl, isopropyl, butyl, isobutyl, pentyl, isopentyl, hexyl.

Examples of lower alkoxy are methoxy, ethoxy, propoxy, isopropoxy, butoxy, isobutoxy, pentoxy, isopentoxy, hexoxy and isohexoxy.

Halogen is preferably fluorine, chlorine or bromine.

When used herein "aryl" means an aromatic radical having 6 to 12 carbon atoms (e.g. phenyl or naphthyl) which optionally may be substituted by one or more substituents such as lower alkyl, lower alkoxy, halogen halo(lower)alkyl, halo(lower)alkoxy, nitro, amino(lower)alkylamino or di(lower)alkylamino.

Preferably aryloxy is phenoxy, aryl(lower)alkoxy is benzyloxy, halo(lower)alkyl is trifluoromethyl and halo(lower)alkoxy is trifluoromethoxy.

Preferably the compounds of the invention contain a single substituent R in the 8-position of the tetralin ring. Preferred substituents are hydroxy, lower alkoxy (e.g. methoxy) or halogen (e.g. fluorine).

The compounds of the invention may be prepared by reductive amination of a tetralone of formula

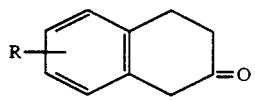
(II)

(where R has the meaning given above) with azetidine

(III)

The above reductive amination process may be carried out in two steps i.e. reacting the tetralone with azetidine and isolating and reducing the intermediate enamine compound or alternatively reacting the tetralone with the azetidine and reducing as a one-pot process without isolating any intermediate.

The reaction of the tetralone with azetidine may be carried out in an inert organic solvent. If necessary the reaction can be carried out in presence of an acid catalyst and/or a dehydrating agent e.g. p-toluene sulphonic acid or titanium (IV) chloride.

The reduction process may be carried out, for example, by catalytic hydrogenation; with a hydride reducing agent (e.g. lithium aluminium hydride, sodium borohydride, sodium cyanoborohydride, tetrabutylammonium cyanoborohydride) which may require the presence of at least one equivalent of acid; or with formic acid.

In the compounds of formula I a substituent R may be converted into another substituent R by methods known in the art. For example, a nitro group may be reduced to an amino group, an amino group may be alkylated to a (lower)alkylamino or di(lower)alkylamino group or acylated to an acylamino group, an ether group such as (lower)alkoxy or aryl(lower)alkoxy may be cleaved to a hydroxy group or a hydroxy group may be etherified to an ether group such as lower alkoxy or aryl(lower)alkoxy.

The processes described above may be carried out to give a compound of the invention in the form of a free base or as an acid addition salt. If the compound of the invention is obtained as an acid addition salt, the free base can be obtained by basifying a solution of the acid addition salt. Conversely, if the product of the process is a free base an acid addition salt, particularly a pharmaceutically acceptable acid addition salt, may be obtained by dissolving the free base in a suitable organic solvent and treating the solution with an acid, in accordance with conventional procedures for preparing acid addition salts from base compounds.

Examples of acid addition salts are those formed from inorganic and organic acids, such as sulphuric, hydrochloric, hydrobromic, phosphoric, tartaric, fumaric, maleic, citric, acetic, formic, methanesulphonic, p-toluenesulphonic, oxalic and succinic acids.

The compounds of the invention contain an asymmetric carbon atom, so that the compounds can exist in different steroisomeric forms. The compounds can be for example, racemates or optically active forms. The optically active forms can be obtained by resolution of the racemates or by asymmetric synthesis.

The compounds of the invention possess pharmacological activity and hence can be used as medicaments. In particular the compounds possess hypotensive activity. The compounds are tested for hypotensive activity in anaesthetised normotensive rats. In this procedure adult male Sprague-Dawley rats weighing 200–400 g are anaesthetised with 70 mg/kg pentobarbitone sodium, i.p. The fermoral (or jugular) vein, the femoral (or carotid) artery, and the trachea are cannulated and the vascular canulae then flushed with 0.3 ml of heparinised saline (125 U/ml). The arterial blood pressure and heart rate are continuously monitored. Top-up doses of 6 or 12 mg/kg anaesthetic are administered as required until a stable base-line is obtained. A cumulative dose-response curve to the test compound is then obtained, using a 5 min dose interval. Each dose is administered in a volume of 1 mg/kg and flushed in with 0.5 ml saline. Systolic, diastolic, and mean arterial blood pressure and heart rate are then calculated 5 min after each dose and compared with the pre-dose value. Mean results from six rats are analysed using analysis of variants. The $ED_{20}$ (ie the dose giving a 20% fall in mean arterial blood pressure) is also calculated. When tested by this procedure 7-(1-azetidinyl)-5,6,7, 8-tetrahydro 1-naphthalenol, a representative compound of the invention, produced dose-related falls in blood pressure and heart rate. The minimum effective dose of this compound which produced a significant decrease in blood pressure was 1 µg/kg iv, and the $ED_{20}$ was 5.2 µg/kg iv.

In pharmacological testing it has been shown that many of the compounds of this invention possess potent $\alpha_2$ agonist effects and/or act upon the central nervous system by binding to 5-HT receptors. In particular many compounds particularly bind to receptors of the 5-HT$_{1A}$ type. They exhibit activity as 5-HT$_{1A}$-agonists. The pharmacological testing indicates that they can be used in the treatment of neuro-psychiatric disorders such as anxiety. Preferred compounds are those of formula (I) in which R is a substituent in the 8-position of the tetralin ring chosen from hydroxy, lower alkoxy (e.g. methoxy) and halogen (fluorine).

The compounds are evaluated for 5-HT$_1$ receptor agonist activity in vivo by measuring their ability to induce the 5-HT behavioural syndrome in rats (A. R. Green, *Neuropharmacology*, 1984, 23 1521). Compounds which induce 5-HT-related behaviours are adjudged to be 'active', and a sequential up-down method (A. W. Kimball, W. T. Burnett, and D. G. Doherty, *Radiation Research*, 1957, 7, 1) is used to determine ED$_{50}$ values for the compounds. The ED$_{50}$ value for 7-(1-azetidinyl)-5,6,7, 8-tetrahydro-1-naphthalenol, a representative compound of the invention, was found to be 0.07 mg/kg iv.

The invention also provides a pharmaceutical composition comprising a compound or a pharmaceutically acceptable acid addition salt thereof in association with a pharmaceutically acceptable carrier. Any suitable carrier known in the art can be used to prepare the pharmaceutical composition. In such a composition, the carrier is generally a solid or liquid or a mixture of a solid or liquid.

Solid form compositions include powders, granules, tablets, capsules (e.g. hard and soft gelatine capsules), suppositories and pessaries. A solid carrier can be, for example, one or more substances which may also act as flavouring agents, lubricants, solubilisers, suspending agents, fillers, glidants, compression aides, binders or tablet-disintegrating agents; it can also be an encapsulating material. In powders the carrier is a finely divided solid which is in admixture with the finely divided active ingredient. In tablets the active ingredient is mixed with a carrier having the necessary compression properties in suitable proportions and compacted in the shape and size desired. The powders and tablets preferably contain up to 99%, e.g. from 0.03 to 99%. preferably 1 to 80% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

The term "composition" is intended to include the formulation of an active ingredient with encapsulating material as carrier to give a capsule in which the active ingredient (with or without other carriers) is surrounded by the carrier, which is thus in association with it. Similarly cachets are included.

Liquid form compositions include, for example, solutions, suspensions, emulsions, syrups, elixirs and pressurised compositions. The active ingredient, for example, can be dissolved or suspended in a pharmaceutically acceptable liquid carrier such as water, an organic solvent, a mixture of both or pharmaceutically acceptable oils or fats. The liquid carrier can contain other suitable pharmaceutical additives such as solubilisers, emulsifiers, buffers, preservatives, sweetners, flavouring agents, suspending agents, thickening agents, colours, viscosity regulators, stabilisers or osmo-regulators. Suitable examples of liquid carriers for oral and parenteral administration include water (particularly containing additives as above, e.g. cellulose derivatives, preferably sodium carboxymethyl cellulose solution, alcohols, e.g. glycerol and glycols) and their derivatives, and oils (e.g. fractionated coconut oil and arachis oil). For parenteral administration the carrier can also be an oily ester such as ethyl oleate and isopropyl myristate. Sterile liquid carriers are used in sterile liquid form compositions for parenteral administration.

Liquid pharmaceutical compositions which are sterile solutions or suspensions can be utilized by, for example, intramuscular, intraperitoneal or subcutaneous injection. Sterile solutions can also be administered intravenously. When the compound is orally active it can be administered orally either in liquid or solid composition form.

Preferably the pharmaceutical composition is in unit dosage form e.g. as tablets or capsules. In such form, the composition is sub-divided in unit dose containing appropriate quantities of the active ingredient; the unit dosage forms can be packaged composition, for example packeted powders, vials, ampoules, prefilled syringes or sachets containing liquid. The unit dosage form can be, for example, a capsule or tablet itself, or it can be the appropriate number of any such compositions in package form. The quantity of the active ingredient in unit dose of composition may be varied or adjusted from 0.5 mg or less to 750 mg or more, according to the particular need and the activity of the active ingredient.

The following Examples illustrate the invention:

EXAMPLE 1

1-(1,2,3,4-Tetrahydro-2-naphthalenyl)azetidine

Step 1 1-(3,4-Dihydro-2-naphthalenyl)azetidine

A solution of azetidine (6.8 g, 0.12 mol), 3,4-dihydro-2(1 H)-naphthalenone (14.6 g, 0.10 mol), and p-toluenesulphonic acid (1.5 g) in dichloromethane (200 ml) was heated under reflux for 3 h in an apparatus fitted for the continuous removal of water, cooled to room temperature, washed with dilute aqueous sodium carbonate, dried (MgSO$_4$), and evaporated in vacuo to give the product as an oil.

Step 2 1-(1,2,3,4-Tetrahydro-2-naphthalenyl)azetidine

The crude product from Step 1 was dissolved in methanol (1 litre) and reduced at room temperature over platinum oxide (5 g) with hydrogen at 120 p.s.i. (about $8.3 \times 10^5$ Pa). After 2½ h, the solution was filtered and evaporated in vacuo. The residue was purified by chromatography (silica; methanol) to give the product (2.5 g as an oil).

The maleic acid salt was prepared in and crystalised from hot propan-2-ol as colourless crystals, m.p. 139°–141° C.

Found C, 66.8; H, 7.0; N, 4.45; $C_{13}H_{17}N.C_4H_4O_4$ requires C, 67.3; H, 7.0; N, 4.6%

EXAMPLE 2

1-(8-Fluoro-1,2,3,4-tetrahydro-2-naphthalenyl)azetidine

The title compound was prepared from 8-fluoro-3,4-dihydro-2(1H)-napthalenone (made from 2-fluorophenylacetic acid and ethylene by the method of D. C. Hunden, *Org. Prep. Proced. Int.*, 1984, 16, 294) following the steps outlined in Example 1.

The maleic acid salt had m.p. 139°–141° C.

Found: C, 63.6; H, 6.4; N, 4.2; $C_{13}H_{16}FN.C_4H_4O_4$ requires C, 63.5; H, 6.3; N, 4.4%

EXAMPLE 3

7-(1-Azetidinyl)-5,6,7,8-tetrahydro-1-naphthalenol

This title compound was prepared from 3,4-dihydro-8-hydroxy-2(1H)-naphthalenone following the steps outlined in Example 1. The crude product was not purified by chromatography but was partitioned between ether and dilute hydrochloric acid. The aqueous phase was filtered (to remove unwanted tarry material), washed with ether, basified with concentrated aqueous ammonia, and extracted with ether. The extract was washed with water, dried ($Na_2SO_4$), and evaporated in vacuo to give the product as a buff-coloured solid.

The maleic acid salt had m.p. 188°–190°.

Found: C, 63.9; H, 6.6; N, 4.4; $C_{13}H_{17}NO.C_4H_4O_4$ requires C, 63.9; H, 6.6; N, 4.4%

EXAMPLE 4

1-(1,2,3,4-Tetrahydro-8-methoxy-2-naphthalenyl)-azetidine

The product of Example 3 in free base form (0.8 g, 3.9 mmol) was dissolved in dimethylformamide (20 ml) and treated with 1 N-NaOH (3.9 ml) and methyl p-toluenesulphonate (0.9 g, 4.8 mmol). After 3 h, the solution was poured into water (100 ml) and the mixture extracted with dichloromethane (2×100 ml). The extracts were washed with water (100 ml), dried ($MgSO_4$), and evaporated in vacuo to give an oil.

The oxalic acid salt had m.p. 94°–96° C.

I claim:

1. A compound of formula (I)

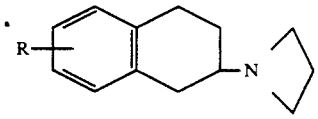

or a pharmaceutically acceptable acid addition salt thereof, wherein R is hydrogen or one or more same or different substitutents selected from hydroxy, lower alkyl, aryl(lower)alkyl, lower alkoxy, aryl(lower)alkoxy, halogen, halo(lower)alkyl, halo(lower)alkoxy, methylenedioxy, nitro, lower alkylcarbonyloxy, aryl(lower)alkylcarbonyloxy, lower alkoxycarbonyl, aminocarbonyl, amino, (lower)alkylamino, di(lower)alkylamino or acylamino.

2. A compound of claim 1 which is 1-(1,2,3,4-tetrahydro-2-naphthalenyl)azetidine or a pharmaceutically acceptable acid addition salt thereof.

3. A compound of claim 1 which is 1-(8-fluoro-1,2,3,4-tetrahydro-2-naphthalenyl)-azetidine or a pharmaceutically acceptable acid addition salt thereof.

4. A compound of claim 1 which is 7-(1-azetidinyl)-5,6,7,8 tetrahydro-1-naphthalenol or a pharmaceutically acceptable acid addition salt thereof.

5. A compound of claim 1 which is 1-(1,2,3,4-tetrahydro-8-methoxy-2-naphthalenyl)azetidine or a pharmaceutically acceptable acid addition salt thereof.

6. A pharmaceutical composition having hypotensive activity comprising a compound as claimed in claim 1 in association with a pharmaceutically acceptable carrier.

* * * * *